（12）United States Patent
Koch et al.

(10) Patent No.: US 10,228,159 B2
(45) Date of Patent: Mar. 12, 2019

(54) HEATER FOR AN INCUBATOR FOR INFANTS AND INCUBATOR FOR INFANTS

(71) Applicant: Drägerwerk AG & Co. KGaA, Lübeck (DE)

(72) Inventors: Jochim Koch, Ratzeburg (DE); Robert Lischinski, Einhaus (DE); Uwe Schmid, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 693 days.

(21) Appl. No.: 14/760,537

(22) PCT Filed: Jan. 10, 2014

(86) PCT No.: PCT/DE2014/000010
§ 371 (c)(1),
(2) Date: Jul. 13, 2015

(87) PCT Pub. No.: WO2014/108126
PCT Pub. Date: Jul. 17, 2014

(65) Prior Publication Data
US 2015/0354853 A1    Dec. 10, 2015

(30) Foreign Application Priority Data

Jan. 14, 2013 (DE) ........................ 10 2013 000 476

(51) Int. Cl.
*A61G 11/00* (2006.01)
*F24H 3/02* (2006.01)
*A61F 7/00* (2006.01)
*A61G 7/005* (2006.01)

(52) U.S. Cl.
CPC ............ *F24H 3/022* (2013.01); *A61F 7/0053* (2013.01); *A61G 11/00* (2013.01); *A61F 2007/0055* (2013.01); *A61G 7/005* (2013.01)

(58) Field of Classification Search
CPC ............ A61F 2007/0055; A61F 7/0053; A61F 7/007; A61F 7/0085; A61G 11/003
See application file for complete search history.

(56) References Cited

U.S. PATENT DOCUMENTS 4,796,605 A    1/1989 Sasaki et al.
5,616,115 A    4/1997 Gloyd et al.
(Continued)

FOREIGN PATENT DOCUMENTS

DE    34 19 001 A1    11/1985
DE    197 30 834 A1    1/1999
(Continued)

*Primary Examiner* — Christopher H Matthews
(74) *Attorney, Agent, or Firm* — McGlew and Tuttle, P.C.

(57) ABSTRACT

A heater, for an incubator for infants, has a housing structure with an upper housing surface and a lower housing surface, at least one air inlet for an inflowing air stream, at least one air outlet for an outflowing air stream, at least one fan impeller, at least one heating element and at least one heat transfer element. The upper housing surface and the lower housing surface delimit a flow space. The heat transfer element is a plate with a flat surface that is arranged horizontally during operation of the heater. An incubator for infants having such a heater is also provided.

1 Claim, 5 Drawing Sheets

(56) References Cited

U.S. PATENT DOCUMENTS

| | | | |
|---|---|---|---|
| 5,707,006 A * | 1/1998 | Skulic | A61G 11/00 |
| | | | 219/543 |
| 5,935,055 A | 8/1999 | Koch et al. | |
| 6,428,465 B1 | 8/2002 | Belsinger, Jr. | |
| 2013/0204074 A1* | 8/2013 | Belval | A61G 11/00 |
| | | | 600/22 |

FOREIGN PATENT DOCUMENTS

| | | |
|---|---|---|
| JP | H07-328077 A | 12/1995 |
| WO | 98/48755 A1 | 11/1998 |

\* cited by examiner

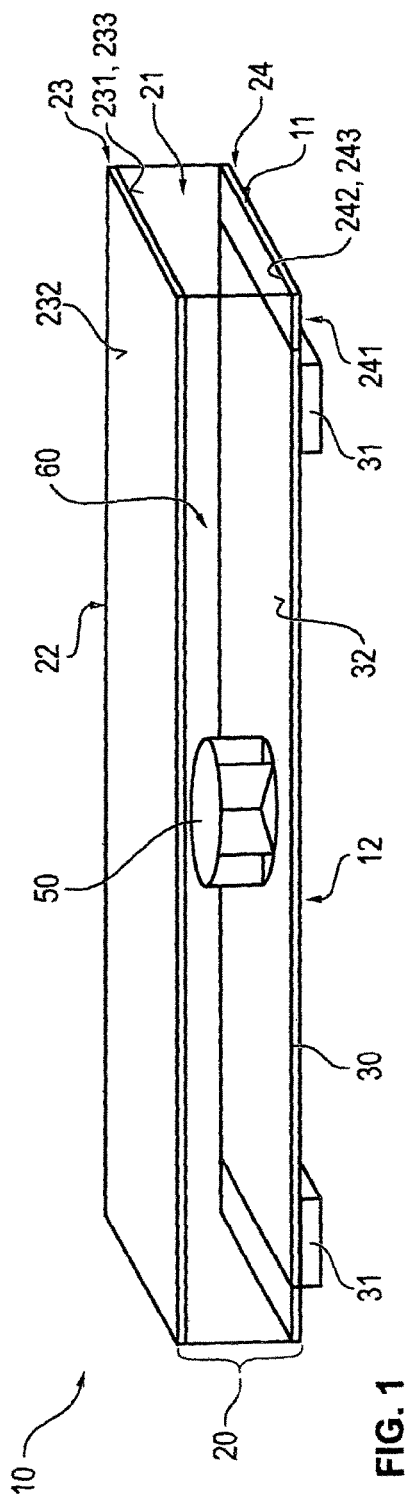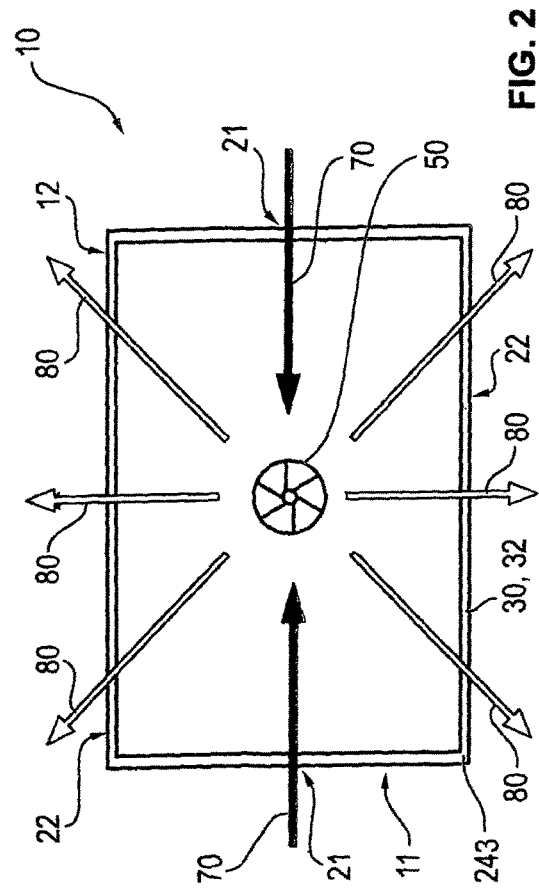

HEATER FOR AN INCUBATOR FOR INFANTS AND INCUBATOR FOR INFANTS

CROSS REFERENCE TO RELATED APPLICATIONS

This application is a United States National Phase Application of International Application PCT/DE2014/000010 filed Jan. 10, 2014 and claims the benefit of priority under 35 U.S.C. § 119 of German Patent Application DE 10 2013 000 476.4 filed Jan. 14, 2013, the entire contents of which are incorporated herein by reference.

FIELD OF THE INVENTION

The present invention pertains to a heater for an incubator for infants, wherein the heater has a housing structure with an upper housing surface and with a lower housing surface, at least one air inlet for an inflowing air stream, at least one air outlet for an outflowing air stream, at least one fan impeller, at least one heating element and at least one heat transfer element, as well as to an incubator for infants with such a heater.

BACKGROUND OF THE INVENTION

Incubators for infants, especially for newborn and premature babies (neonates), are generally known. They play an important role above all in the area of intensive care, for example, in supporting the developmental and growth processes of newborn babies. It is usually ensured by means of such incubators that the infant to be treated is exposed to controlled environmental conditions. Incubators according to the present invention are also called thermotherapy devices. Both closed and open devices are known in this connection. Closed devices are usually characterized by the presence of a pivotable or openable covering hood. Such a covering hood is, as a rule, missing in open devices. An existing covering hood can be removed or opened in so-called hybrid devices, so that one and the same device can be operated in both the open care mode and the closed care mode. Regulation of the temperature that prevails in the incubator is especially important in any case. Incubators for infants are therefore usually heated.

The heating of such incubators especially in the closed care mode may be carried out, for example, by means of a convective heater. The incubator or the heater of the incubator usually has a fan impeller for this, which brings about circulation of the air in the interior space. The circulated air in the interior space will then flow over a heat exchanger element before it enters the area in which the infant to be treated is located. Typical heat exchanger elements (heat transfer elements) of such a heater may be, for example, heating coil tubes or rib-like heating elements. However, heating coil tubes, in particular, have not turned out to be optimal by all means in respect to heat transfer, arrangement in the flow duct and cleaning. Attempts have therefore been made to develop different heaters for incubators.

For example, U.S. Pat. No. 6,428,465 provides for an incubator with a heater, in which heater an upper housing part and a lower housing part form a flow duct (flow chamber). This flow duct comprises an upper air chamber and a lower air chamber. The fan impeller is arranged centrally in the heater of the incubator. The air is admitted into the flow duct through air inlet areas, which are located on the front sides of the incubator. The air leaves through air outlet ducts, which are located on the long sides of the incubator. On the whole, an air inlet area is formed in this manner in the lower air chamber, and the air flows in this air inlet area towards the fan impeller, and an air outlet area arranged at right angles thereto is formed in the upper air chamber, in which air outlet area the air flows away from the fan impeller. The fan impeller is arranged at the transition between the lower air chamber and the upper air chamber such that it exerts a drawing-in action on the air stream in the lower air chamber during the operation of the incubator and a blowing-away action on the air stream in the upper air chamber arranged at right angles thereto.

A heat exchanger element, which is provided with a plurality of lamellae, is provided for heating the air stream in U.S. Pat. No. 6,428,465. These lamellae are used to enlarge the heat exchange surface and to increase the flow guiding and extend from the top side of the heat exchanger element more or less vertically upward. The heat exchanger element is arranged in the lower air chamber, i.e., in the air inlet area, in which the inflowing air flows to the fan impeller. The air outlet area is not heated.

U.S. Pat. No. 5,935,055 likewise provides for an improved heater for an incubator with a centrally arranged fan impeller. The air flowing from the incubator chamber into the flow area of the heater flows from the front sides to this central fan impeller and is heated there by means of a likewise central, ring-shaped heat exchanger element. The air is subsequently discharged back into the incubator chamber on the two long sides of the incubator.

It is problematic in both cases that the heater may be able to be cleaned in a very complicated and cumbersome manner due to the relatively complicated geometry of the respective heat exchanger elements, for example, in the area of the lamellae. In particular, there may be areas in the heater which are accessible for complete and proper cleaning with difficulty only.

In addition, it may be necessary to operate the particular heater, especially the particular heat exchanger element, with a relatively high surface temperature in order to guarantee sufficient and uniform heating of the air. The surface temperature may thus, for example, easily and markedly exceed the value of 100° C. This also applies especially to heating coils, which may have a relatively small surface.

Another problem may be represented by the elements inserted into the flow path, for example, the lamellae or the central, ring-shaped heater, from an acoustic point of view. Considerable noise may be generated by these elements.

SUMMARY OF THE INVENTION

Based on this, an object of the present invention is to provide an improved heater for an incubator for infants, which overcomes these and other drawbacks of the state of the art.

Moreover, a corresponding incubator shall be provided for infants with an improved heater. In particular, a heater that can be cleaned in a simple manner and operates with a low noise level shall be provided for an incubator for infants. Furthermore, the heater shall be able to be operated with the lowest possible surface temperature. At the same time, uniform heating of the air shall be possible.

A heater for an incubator for infants is provided, wherein the heater has a housing structure with an upper housing surface and with a lower housing surface, at least one air inlet for an inflowing air stream, at least one air outlet for an outflowing air stream, at least one fan impeller, at least one heating element and at least one heat transfer element. The upper housing surface and the lower housing surface define a flow space. The present invention makes provisions for the heat transfer element to be a plate with a flat surface, which plate is arranged horizontally during the operation of the heater.

A heater in the sense of the present invention may also be called, as an alternative, a heating device or a device for heating the air in the interior space of an incubator for infants.

The heat transfer element is preferably a plate in this case, whose size preferably corresponds entirely or partially to the base of the heater. The base of the heater is the projection area of the heater in case of vertical view from the top on the operating heater, i.e., the heater arranged in the incubator. Furthermore, the shape of the plate corresponds entirely or partially to the shape of the above-mentioned projection area of the heater. The shape of the plate is independent from the size of the plate, i.e., the plate may have the same shape as the projection area of the heater or a different size and vice versa. A corresponding plate has a generally flat, cuboid-like shape with a pair of mutually opposite main surfaces each, with a pair of long side surfaces and with a pair of short side surfaces. The side surfaces are very narrow compared to the main surfaces. The long and short side surfaces may, of course, also have the same length, so that the main surfaces have a more or less square shape. The side surfaces preferably have only the shape of edges, which define the main surfaces. The edges formed by the side surfaces may be angular. However, round or curved transitions between the surfaces are also conceivable. All surfaces may also have curvatures or arches, which may be of equal size or have different sizes. It is conceivable, for example, that the plate is arched such that it has a trough-like shape. A semi-ellipsoidal shape is conceivable as well. In other words, the plate may be an at least partially arched plate with a flat surface, preferably with a surface free from lamellae, as will be described below.

The main surfaces extend in the area of the heater preferably in the horizontal direction, i.e., in parallel to the base of the heater. In any case, the main surface of such a plate, i.e., consequently of the heat transfer element, is designed such and is arranged in the heater such that it can extend in parallel to the reclining surface of an incubator according to the present invention, which will be described below, during the operation of the heater.

In other words, the heat transfer element is plate-shaped preferably with an approximately rectangular main surface with optionally rounded corners and has an essentially unstructured, smooth surface. A "flat surface" or an "essentially unstructured, smooth" surface is defined here such that the heat transfer element has no lamellae or similar projections or elevations. In other words, a flat surface may be a surface that is free from lamellae. In particular, the heat transfer element has no elements that extend upwardly from the base of the heat transfer element and are suitable during the operation of the heater for generating swirling of an air stream flowing over the plate, which leads to flow noises, which are audible to the human ear, especially for newborn babies. The generation of flow noises, which can be perceived by the infant lying in the incubator, can thus be avoided.

It is recognized in this connection that the heat transfer element is preferably free from lamellae. It is especially preferably free from lamellae that are oriented at right angles during the operation of the heater and bring about guiding of the air stream. Such a smooth plate with a flat surface can be wiped off easily and can therefore be cleaned thoroughly. In addition, practically no interfering swirls or noises are thus generated when an air stream flows past over the plate, i.e., the heat transfer element.

The heat transfer element advantageously consists of a material with good thermal conductivity, for example, metal, temperature-resistance plastic with good thermal conductivity or the like. The heat transfer element may be a massive plate, which consists of the heat-conducting material. However, it is also conceivable that the heat transfer element has a hollow core, which can act as a fluid chamber. A heated fluid, for example, water or air, can flow through such a fluid chamber. In any case, the surface of the heat transfer element can be heated, and the heat transfer element has a high thermal conductivity.

It is especially advantageous if the heat transfer element is arranged horizontally during the operation of the heater. Thus, it may be arranged, for example, in parallel to the reclining surface of an incubator, in which the heater is used. Horizontal arrangement of an object is defined in the sense of the present invention such that a geometric body, namely, the object, for example, the heater or the heat transfer element of the heater, which has a three-dimensional shape, which has a main surface, which is larger than the other surfaces of the body, is oriented in space such that this largest surface of the body is directed in parallel to a horizontal plane. Certain angle tolerances, within which the largest surface may be sloped in relation to the horizontal plane, deviating from a strictly parallel orientation, are, of course, conceivable. Such an angle tolerance may be, for example, ±45° or less, ±40° or less, ±35° or less, ±30° or less, ±25° or less, ±20° or less, ±15° or less, ±10° or less, ±5° or less or ±1° or less. However, angle tolerances greater than ±45° are conceivable as well. It is advantageous in this connection if the surface is always oriented such that a reclining surface for an infant, which surface is arranged above the heater in an incubator, can be heated uniformly during the operation of the heater.

The housing structure of the heater may comprise, for example, an upper housing element and a lower housing element. The housing elements are located opposite each other and may be flat or they may be entirely or partially curved. Each housing element has a top side and an underside. The underside of the upper housing element represents the upper housing surface and the top side of the lower housing element represents the lower housing surface. The upper housing surface and the lower housing surface define a space formed between the two housing elements of the housing structure, namely, the flow space.

The upper housing element is, for example, an injection-molded part, which may be arranged under the reclining surface during the use according to the present invention of the heater in the incubator. It may extend from one side wall to an opposite side wall of the incubator in both the longitudinal direction and the transverse direction. However, it is also conceivable that it is smaller.

The lower housing element may be formed entirely or partially by the heat transfer element. For example, it may be simply a metal plate or a plate consisting of another material having good or high thermal conductivity, which is arranged at a certain distance in parallel to the upper plate. It is also conceivable that the lower housing element has a frame in the form of an injection-molded part (injection-molded frame), in which the heat transfer element is held. A continuous injection-molded part, which forms the lower housing element and on which the heat transfer element is arranged, is also conceivable. Both the injection-molded frame and the heat transfer element may extend, just as the upper housing element, from one side wall to an opposite side wall of the incubator both in the longitudinal direction and the transverse direction during the use according to the present invention of the heater.

The heat transfer element may be in heat-conducting contact with one or more heating elements. For example, one or more heating cartridges may be arranged under the heat transfer element. The heat released by the at least one heating element is transferred to the heat transfer element. Due to the preferably very high thermal conductivity of the material of which the heat transfer element consists, or, in other words due to the high thermal conductivity of the heat transfer element, the heat transfer element is heated rapidly and uniformly. The heat transfer element thus heated will in turn release the heat to the air that is in contact with it, for example, to an air stream flowing past over the heat transfer element. The heat may also be fed, for example, through a foil heater, which is bonded on the underside of the heat transfer element. The heat may also be transferred by a heating element applied to the heat transfer element, for example, a thick-layer heater, a thin-layer heater or a film heater. Such a heater can be manufactured, for example, by plasma spraying or even according to another coating method.

The fan impeller is arranged between the upper housing element and the lower housing element. The fan impeller brings about circulation of the air in the flow space of the heater. It can consequently cause an air stream to be generated, which flows along the heat transfer element. The air stream can, moreover, be drawn into the heater, especially into the flow space, through the at least one air inlet. The air stream can also be blown out of the heater, especially the flow space, through the air outlet. In the sense of the present invention, an air stream that flows from the air inlet to the fan impeller is called inflowing air stream, while an air stream that flows from the fan impeller to the air outlet is called outflowing air stream. When the heater is used according to the present invention, the inflowing air stream is air that is returned back to the heater from the area of the incubator, in which the infant to be treated is located (incubator chamber, also called compartment). By contrast, the outflowing air stream is the air that shall be returned as heated air into this area.

The air inlet and the air outlet are openings in the simplest case, for example, slots, which are formed on the sides of the heater between the upper and lower housing elements. For example, such slots can be formed by the upper housing element and the lower housing element being arranged at a certain distance from one another. Other solutions, e.g., recesses in the housing structure or the like, are, of course, also conceivable. The air inlet and the air outlet are preferably arranged in the heater such that both the inflowing air stream and the outflowing air stream are sent over the heat transfer element. This ensures uniform distribution of the heat and facilitates the establishment of a uniform temperature distribution in the incubator chamber.

It is thus recognized that it is especially advantageous if the heat generated by the heating element can be transferred by means of the heat transfer element both to the inflowing air stream and the outflowing air stream. This can be achieved, for example, by the surface of the heat transfer element being so large that both the inflowing air stream and the outflowing air stream flow over the heat transfer element. For example, as was already described above, the heat transfer element may entirely or partially form the lower housing surface. It is especially advantageous in this connection that the heat transfer element has a very large surface. As a consequence, the surface temperatures necessary for the transmission of the output can be lowered to markedly below 100° C. As a consequence, the risk of burns or the undesired generation of odor is markedly reduced.

Provisions are made in an especially advantageous embodiment for the heater to have a flow element. Such a flow element may be used, for example, to make the guiding of the outflowing or inflowing air stream in the heater as optimal as possible. In particular, the flow element may be used to prevent swirling and hence mixing of the inflowing and outflowing air streams.

The flow element is designed, for example, such that it forms a flow guide for the inflowing air stream and for the outflowing air stream. This flow guide preferably causes both swirling and short-circuits to be prevented from developing between the inflowing air stream and the outflowing air stream. In other words, the flow element is designed such that it prevents a short-circuit of the flow between the inflowing air stream and the outflowing air stream. It is especially favorable in this connection if the flow element is arranged between the upper housing surface and the lower housing surface.

The flow element preferably has a top side and an underside. The top side faces the upper housing surface in at least some sections, and the underside faces the lower housing surface. The flow element may also form a part of the upper housing element and hence a part of the upper housing surface. For example, the upper housing element may have a two-part design and comprise a cover element as well as the flow element. The flow element may be made in this case in one piece with the upper housing element and/or with the lower housing element.

The flow element divides the flow space of the heater into an inflow space and an outflow space. The inflow space is the area of the flow space in which the inflowing air stream flows from the air inlet to the fan impeller. The outflow space is the area of the flow space in which the outflowing air stream flows from the fan impeller to the air outlet. The fan impeller may be preferably arranged in this case entirely or partially in the outflow space.

The inflow space is defined at least by the upper housing surface, the lower housing surface and the top side of the flow element. The outflow space is defined at least partially by the underside of the flow element and the lower housing surface. In particular, it is advantageous if the flow element is designed such that it is suitable for guiding the air stream flowing from the air inlet to the fan impeller and to guide at the same time the air stream flowing from the fan impeller to the air outlet. The inflowing air (the inflowing air stream), which is coming, for example, from the incubator chamber, flows from the air inlet through the inflow space to the fan impeller. At the same time, the outflowing air flows again away from the fan impeller through the outflow space to the air outlet and back into the incubator chamber. It is seen that the lower housing surface defines both the inflow space and the outflow space. The heat transfer element can thus also define both the inflow space and the outflow space.

As a consequence, both the inflowing air and the outflowing air also flow over the heat transfer element in this case. The air can be heated very effectively and uniformly in this manner in the entire flow space. In other words, both the underside of the inflow space and the underside of the outflow space may be formed by the heat transfer element. As a consequence, it is sufficient to operate the heat transfer element with a relatively low surface temperature, which may be markedly below 100° C. For example, surface temperatures of 90° C. or lower, 80° C. or lower, 70° C. or lower or even 60° C. or lower are thus conceivable.

It is advantageous, furthermore, if the flow element has at least one passage opening, through which the inflow space and the outflow space are connected with one another for flow. The inflowing air stream reaches through the passage opening the outflow space, in which the fan impeller is preferably arranged. For example, the passage opening may be formed directly above the fan impeller, so that the fan impeller draws the inflowing air through the passage opening into the outflow space.

The flow element preferably forms at least one inflow barrier for the inflowing air stream. The inflowing air stream is sent over the inflow barrier to the passage opening. The inflow barrier is preferably formed by the surface of the flow element. At least one edge of the flow element is in positive-locking contact for this, in at least some sections, with the lower housing surface. Sealing elements may be present on the lower housing surface. The sealing elements may be, for example, projections, whose shape is adapted to the shape of the lower edge of the flow element. The inflowing air stream cannot flow through in this manner between the flow element and the lower housing surface, but is forced to flow over the surface of the flow element. The inflowing air stream is sent automatically to the passage opening.

It is especially advantageous if, as was described above, the lower housing surface is formed by the heat transfer element of the heater. The inflowing air stream is already heated in this manner during the inflow and flows as a preheated air stream over the surface of the flow element to the fan impeller, i.e., to the outflow space.

Furthermore, the flow element preferably forms at least one outflow guide for the outflowing air stream. The outflow guide is preferably defined by the underside of the flow element as well as by the lower housing surface, preferably by the heat transfer element. The flow element is preferably arched now in such a way that it is in positive-locking, tight contact with the lower housing surface at the above-mentioned inflow barriers. By contrast, a gap is formed between the lower housing surface and the flow element in the area of the outflow guides. The outflow guide is preferably arranged at right angles to the inflow barrier. The outflowing air stream can then escape through the gap between the flow element and the lower housing surface and then flow out of the heater through the air outlet and flow, for example, into the incubator chamber. The flow element may, of course, also have a plurality of inflow barriers and/or a plurality of outflow guides. Regardless of the number of the inflow barriers and outflow guides, the flow element is always designed such that a short-circuit of flow can be avoided between the inflowing air stream flowing along the inflow barrier or inflow barriers and the outflowing air stream flowing along the outflow guide or guides.

The above-described flow element may also have a fastening section in a preferred embodiment variant. This is especially advantageous when the flow element forms, as was described above, a part of the upper housing element. The fastening section preferably extends in parallel to the lower housing surface to the edge of the heater. The fastening section of the flow element may be, for example, an area of the flow element that extends to one or more side walls of the incubator. For example, the upper housing element may have such a two-part design that it has the flow element and additionally a cover element. Both the flow element and the cover element will now have each a top side and an underside. The upper housing element is preferably designed now such that the underside of the flow element and the underside of the cover element form the upper housing surface, which defines the flow space.

The inflow space may have two sections in such an embodiment. The first section is defined by the underside of the flow element and the lower housing surface, i.e., the heat transfer element. The second section is defined by the top side of the flow element and the upper housing surface. At least one additional passage opening, through which the inflowing air stream can flow from the first section of the inflow space into the second section of the inflow space, can now be formed in the flow element. An inflow barrier each, as it was described above, is formed in the area of such an additional passage opening. The inflowing air stream now flows, for example, first through the first section and is preheated by the heat transfer element in the process. It then flows further along the surface of the flow element over the inflow barrier through the additional passage opening into the second section. The passage opening, which connects the inflow space and the outflow space with one another, is then formed in the area of the second section. The inflowing air stream finally flows through this passage opening into the outflow space.

It is consequently seen that the inflow space may have one section or a plurality of sections. An inflow space, which comprises only one section, is defined now by the lower housing surface, the top side of the flow element and the upper housing surface. In an inflow space, which comprises a plurality of sections, a first section is preferably defined by the lower housing surface and the underside of the flow element, namely, in the area of the fastening section of the flow element, and a second section is defined by the top side of the flow element and the upper housing surface.

Regardless of the concrete embodiment of the housing structure, it is advantageous if the air guiding in the heater, i.e., the guiding of the inflowing and outflowing air streams, is designed such as to be symmetrical. For example, an inflowing air stream each may flow into the heater from two mutually opposite sides. At the same time, an outflowing air stream each can leave the heater on two likewise mutually opposite sides, which are, however, arranged at right angles to the aforementioned sides. It is advantageous in this connection if the fan impeller is arranged centrally in the heater. If a flow element is present, this is preferably also arranged centrally in the heater. The inflow barriers and the outflow guides, if present, are preferably also of a symmetrical design.

In another preferred embodiment, the above-described heater according to the present invention has a heated water of condensation collection site. It may be a slight curvature of the lower housing surface. This curvature may represent, for example, the lowest geometric point of the outflow space. Water of condensation, which may be formed on the side walls in case of high humidity and possibly flow into the lower housing, may collect in this lowest geometric point. Such water of condensation usually has an unhygienic potential, because microorganisms may grow in the liquid. However, this is counteracted by means of the water of condensation collection site according to the present invention, because the water of condensation is heated again by the heat transfer element and evaporated as a result. The growth of microorganisms is thus effectively prevented, and microorganisms may possibly also be killed directly.

In a further aspect, the present invention pertains to an incubator for infants with an above-described heater according to the present invention, wherein the incubator has an incubator chamber and a reclining surface. An incubator is defined in the sense of the present invention as a closed care unit or as a hybrid care unit, which can be used for both open care and closed care. Such a care unit typically has a reclining surface, which is enclosed by side walls. The incubator has, furthermore, a covering hood, which may be able to be removed, displaced or pivoted in case of hybrid care units. The reclining surface and the side walls form the incubator chamber, which is defined upwardly by the covering hood in the closed operation. The reclining surface always forms the bottom of the incubator chamber and consequently the lower limitation of the incubation chamber. The above-described heater according to the present invention is arranged under the incubator chamber in an incubator according to the present invention. Not only the heat transfer element, but the entire heater is preferably arranged horizontally. A horizontal arrangement is defined here as well such that a geometric body, namely, the object, for example, the heater or the heat transfer element of the heater, which has a three-dimensional shape, has a main surface, which is larger than the other surfaces of the body, is oriented in space such that this largest surface of the body is oriented in parallel to a horizontal plane. Certain angle tolerances, as they were described above, within which the largest surface may be sloped in relation to the horizontal plane, deviating from a strictly parallel orientation, are, of course, conceivable in this case as well.

It is especially advantageous in this case if the upper housing element of the heater is arranged under the reclining surface. The heater heats in this manner not only the air stream flowing through the housing construction, but it also radiates heat directly onto the reclining surface. Not only can thus the ambient air within the incubator chamber be advantageously heated and controlled, but the reclining surface, on which the infant lies, can also be brought to an advantageous temperature.

It is likewise advantageous in this sense if the heater is arranged in parallel to the reclining surface. The reclining surface can be heated very uniformly in this manner. The reclining surface may also be brought into an oblique position within certain limits for therapeutic purposes, for example, Trendelenburg or anti-Trendelenburg positioning. However, the position of the heater does not change now, but it remains parallel to the horizontal starting position of the reclining surface. It is also conceivable that the distance between the reclining surface and the heater is variable. For example, the reclining surface may be raised or lowered for the care of the infant located thereon, without the position of the heater being changed.

Provisions are made in another advantageous embodiment for the above-described incubator to have a base with a length L and a width B, wherein the length l and the width b of the surface of the heat transfer element of the heater essentially correspond to the size of the length and width of the base of the incubator. The base of the incubator is again defined here as the projection area of the incubator in a vertical top view. It is seen that the heat transfer element of the heater extends essentially over the entire base of the incubator. The heat transfer element itself can bring about in this manner a sufficient and uniform heating of the reclining surface and of the air in the incubator.

Furthermore, provisions may be made for suction slots to be formed for feeding the inflowing air stream from the incubator chamber for heating on two mutually opposite first sides of the reclining surface, and for air slots to be formed on two mutually opposite sides of the reclining surface for feeding the outflowing air stream from the heater into the incubator chamber. For example, the mutually opposite first sides of the reclining surface may be the front sides of the incubator, and the two mutually opposite second sides may be the longitudinal sides of the incubator, which are arranged at right angles to these front sides.

An especially advantageous air guiding within the incubator can now be described as follows: The air present in the incubator flows through the suction slots from the incubator chamber into the area of the heater. The air flows there as inflowing air stream through the air inlet and into the flow space, especially into the inflow space. The inflowing air stream is guided in the inflow space over the lower housing surface, i.e., over the surface of the heat transfer element, to the inflow barrier or barriers. The inflowing air stream is heated in the process. The inflowing air stream is guided from the inflow barrier or inflow barriers further over the surface of the flow elements through the passage opening to the fan impeller. The inflowing air stream, when flowing along the inflow barriers, may now flow through the additional passage openings, if these are present. When passing through the passage opening, which connects the inflow space and the outflow space with one another, the inflowing air stream reaches the fan impeller. The inflowing air stream now becomes an outflowing air stream. The now outflowing air as an outflowing air stream is guided now by the fan impeller likewise over the lower housing surface along the underside of the flow element to the outflow guide and from there to the air outlet. The outflowing air stream is also heated in the process. The outflowing air flows again from the air outlet through the air slots back into the incubator chamber. The air thus heated may rise upward in the manner of a curtain in the incubator chamber, for example, at the side walls of the incubator chamber. The air may again cool slightly while rising upward. The cooling air will then again flow at the ceiling of the incubator chamber, i.e., for example, along the covering hood, to the side surfaces, on which it shall again be drawn into the heater and will sink again. This sinking air stream would now be returned again to the heater through the suction slots and the cycle starts anew.

Further features, details and advantages of the present invention appear from the text of the claims as well as from the following description of exemplary embodiments on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic view of a heater according to the present invention for an incubator for infants;

FIG. 2 is a schematic top view of the lower housing surface of the heater according to the present invention according to FIG. 1 with a schematic view of the inflowing and outflowing air stream;

FIG. 5a is the schematic flow path of an inflowing air stream in an incubator corresponding to FIG. 4a;

FIG. 5b is the schematic flow path of an outflowing air stream in an incubator according to the present invention corresponding to 4b.

DESCRIPTION OF THE PREFERRED EMBODIMENTS

Figure 3:
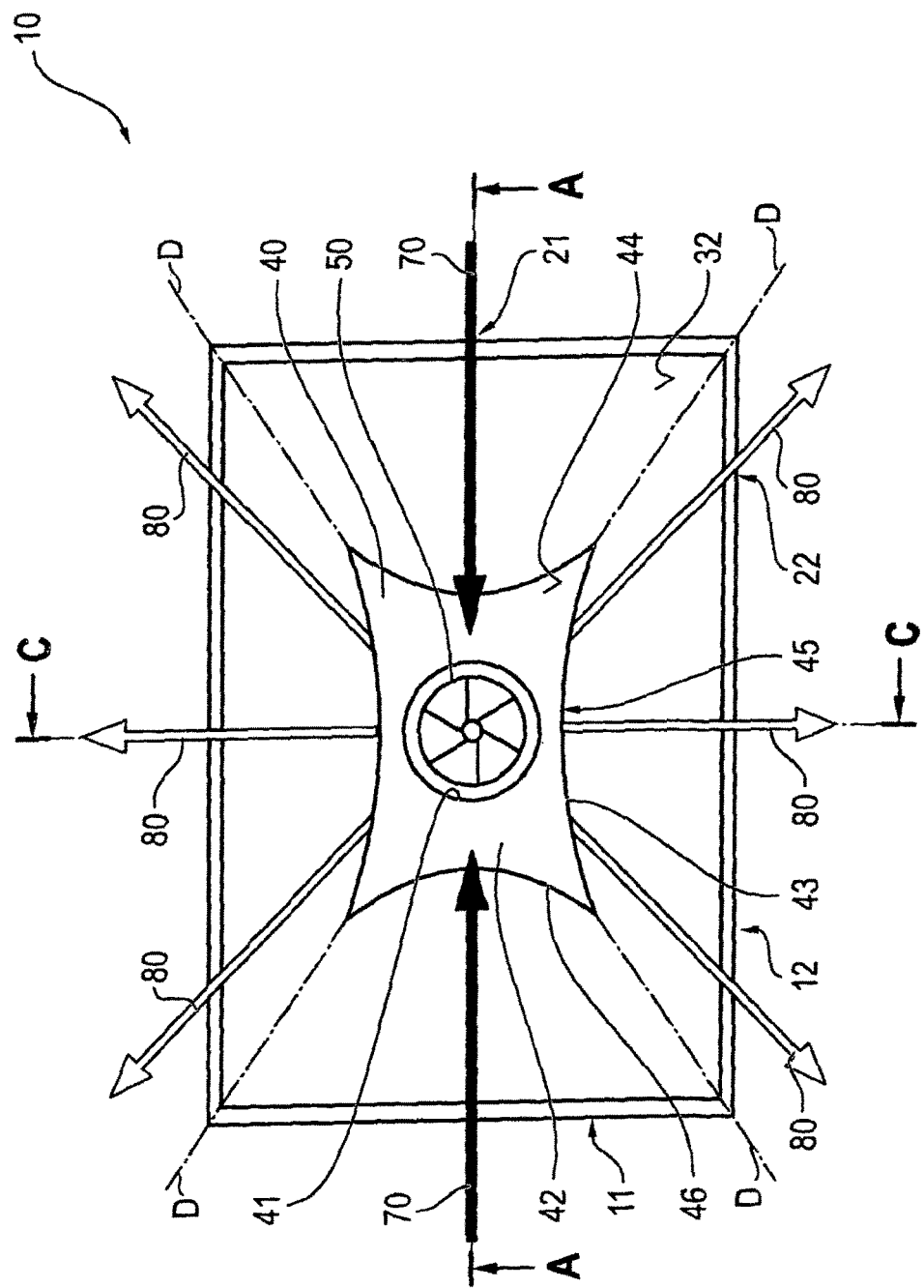
FIG. 3 is a schematic top view of s lower housing surface of another embodiment of a heater according to the present invention with flow element.

Referring to the drawings, it is seen in FIG. 1 that a heater 10 according to the present invention comprises a housing structure 20 with an upper housing element 23 and with a lower housing element 24. The upper housing element 23 has an underside 231 and a top side 232. The underside 231 of the upper housing element 23 forms an upper housing surface 233. The lower housing element 24 has an underside 241 and a top side 242. The top side 242 of the lower housing element 24 forms a lower housing surface 243. The lower housing surface 243 may extend, as in the schematic example being shown, along the entire top side 242 of the lower housing element 24. However, it is also conceivable that the lower housing surface 243 extends only along a section of the lower housing element 24. The upper housing surface 233 may extend now, as in the schematic example being shown, along the entire underside 231 of the upper housing element 23. It is, however, also conceivable that the upper housing surface 233 extends only along a section of the upper housing element 24.

The upper housing surface 233 and the lower housing surface 243 define a flow space 60. The upper housing surface 233 defines the flow space 60 from above and the lower housing surface 243 defines the flow space 60 from below during the operation of the heater. The upper housing surface 233, i.e., consequently the underside 231 of the upper housing element 23, could consequently also be called "upper surface 233, which defines the flow space 60." The lower housing surface 243, i.e., consequently the top side 232 of the lower housing element 24, could consequently also be called "lower surface 243, which defines the flow space 60."

The heat transfer element 30 is arranged at the lower housing surface 243. Two heating elements 31 are arranged under the heat transfer element 30 in the example being shown. These are in heat-conducting contact with the heat transfer element 30. However, it is also conceivable that a heater 10 according to the present invention may have only one heating element 31. More than two heating elements 31 may be present as well. The heating element or heating elements 31 may also have a planiform design. The heat transfer element 30 is planiform and has a flat surface 32. The heat transfer element 30 is arranged horizontally during the operation of the heater 10.

Furthermore, a fan impeller 50 is arranged in the flow space 60. This fan impeller is arranged centrally on the heat transfer element 30 in the example being shown. However, it is also conceivable that the fan impeller 50 is arranged non-centrally on one of the sides of the housing structure 20.

The heater 10 according to the present invention has, furthermore, an air inlet 21 and an air outlet 22. The air inlet 21 is formed on a first side 11 of the housing structure 20. The air outlet 22 is formed on a second side 12 of the housing structure 20. The side 11 on which the air inlet 21 is formed and the side 12 on which the air outlet 22 is formed are oriented at right angles in relation to one another.

It is seen, furthermore, in FIG. 1 that the heat transfer element 30 forms entirely or partially the lower housing surface 243. In particular, the surface 32 of the heat transfer element 30 forms a part of the lower housing surface 243. The heat transfer element 30 may extend now, as can be seen in the example being shown, up to a short distance in front of the edge of the side 11 or even up to the very edge of the side 12 or vice versa. The heat transfer element 30 may, of course, also extend in a variant, not shown, to the edge of the lower housing element 24 on both sides, or a distance can be formed to the edge of the housing element 24 on both sides.

It is seen in FIG. 2 that both the inflowing air stream 70 and the outflowing air stream 80 are guided over the surface 32 of the heat transfer element 30, i.e., consequently over the lower housing surface 243. In particular, it is seen in FIG. 2 that the heat transfer element 30 almost completely fills the lower housing surface 243 of the heater 10 according to the present invention. A fan impeller 50 is arranged in the center of the heat transfer element 30 in this case as well. The air inlet 21 is located on the narrow side 11 of the heater 10 according to the present invention. This narrow side 11 may be oriented, for example, toward the front side of the incubator 100 according to the present invention during the operation of the heater (cf. FIGS. 4a, 4b, 5a, 5b). The air outlet 22 is formed on the long side 12 of the heater 10 according to the present invention. This side 12 may correspond, for example, to the longitudinal side of the incubator according to the present invention. It is seen that the inflowing air stream 70 and the outflowing air stream 80 are formed symmetrically. A further detailed representation of air streams in an incubator 100 according to the present invention or in a heater 10 according to the present invention is shown in FIGS. 5a and 5b.

FIG. 3 shows another schematic functional diagram for an exemplary embodiment of the heater 10 according to the present invention. FIG. 3 likewise shows a top view of the lower housing surface 243, which was already described above in connection with FIGS. 1 and 2 for the housing structure 20 of the heater 10 according to the present invention, which housing structure was likewise already described above. The heat transfer element 30 also occupies essentially the entire surface of the lower housing surface 243 in this case, so that the surface 32 forms a part of the lower housing surface 243. A fan impeller 50 is arranged centrally. It is, further, seen in FIG. 3 that the heater 10 according to the present invention, which is shown there, has a flow element 40. This flow element 40 is arranged centrally above the heat transfer element 30. However, it may also be arranged non-centrally.

The flow element 40 has a passage opening 41, a first edge 46 and a second edge 47. The flow element 40 shown has a symmetrical design, so that it has two first edges 46 and two second edges 47 each. It is also conceivable that the flow element 40 has an asymmetric shape, in which case the flow element 40 may have only one, two or more first edges 46 and/or two edges 47. The shape of the flow element 40 is therefore shown only schematically in these figures (cf. FIGS. 3, 4a, 4b, 5a, 5b, 6) in order to explain the mode of operation of the flow element 40.

In any case, the shape, number and extension of the edges 46 and 47 are adapted to the heater 10 such that there is no short-circuit between the inflowing air stream 70 and the outflowing air stream 80. The flow element 40 is consequently designed such that it does not form a flow guide for the inflowing air stream 70 and for the outflowing air stream 80. This flow guiding preferably causes both swirling and short-circuits to be prevented from occurring between the inflowing air stream 70 and the outflowing air stream 80. In other words, the flow element 40 is designed such that it prevents a flow short-circuit between the inflowing air stream 70 and the outflowing air stream 80. The edges 46, 47 of the flow element 40 may extend now, for example, from the center of the heater 10 along one diagonal or along both diagonals D of the heat transfer element 30. They may extend along the entire diagonal D or only along one part of the diagonal D. At least the edge 46 preferably extends along the entire diagonal D.

The first edge 46 is in sealing contact with the heat transfer element 30. The surface 44 of the flow element forms in this manner an inflow barrier 42 for the inflowing air stream 70. This inflowing air stream 70 is consequently guided, arriving from the air inlet 21, over the surface 32 of the heat transfer element 30 and over the surface 44 of the flow element 40 to the passage opening 41.

The edge 47 has no contact with the surface 32 of the heat transfer element 30. An opening is thus formed between the flow element 40 and the heat transfer element 30. This opening represents an outflow guide 43 for the outflowing air stream 80. The outflowing air stream 80 arrives from the passage opening 41 to the fan impeller 50 and is guided from there over the surface 32 of the heat transfer element 30 and through the outflow guide 43 to the air outlet 22. The air outlet 22 is arranged on the side 12. It is seen that both the inflowing air stream 70 and the outflowing air stream 80 are guided over the surface 32 of the heat transfer element 30. The flow element 40 ensures now that no undesired swirling of the inflowing air stream 70 and of the outflowing air stream 80 will develop. The heater 10 according to the present invention operates in this manner with an especially low noise level. At the same time, the surface 32 of the heat transfer element 30 may have a relatively low temperature, for example, lower than 100° C. The inflowing air stream 70 is already preheated before it reaches the fan impeller 50 through the passage opening 41. As a consequence, the outflowing air stream 80 needs to absorb only a small amount of heat output to reach the desired temperature. It can therefore be heated to the desired air temperature by means of a relatively low surface temperature of the surface 32 before it will again leave the heater 10 through the air outlet 22.

Figure 4:
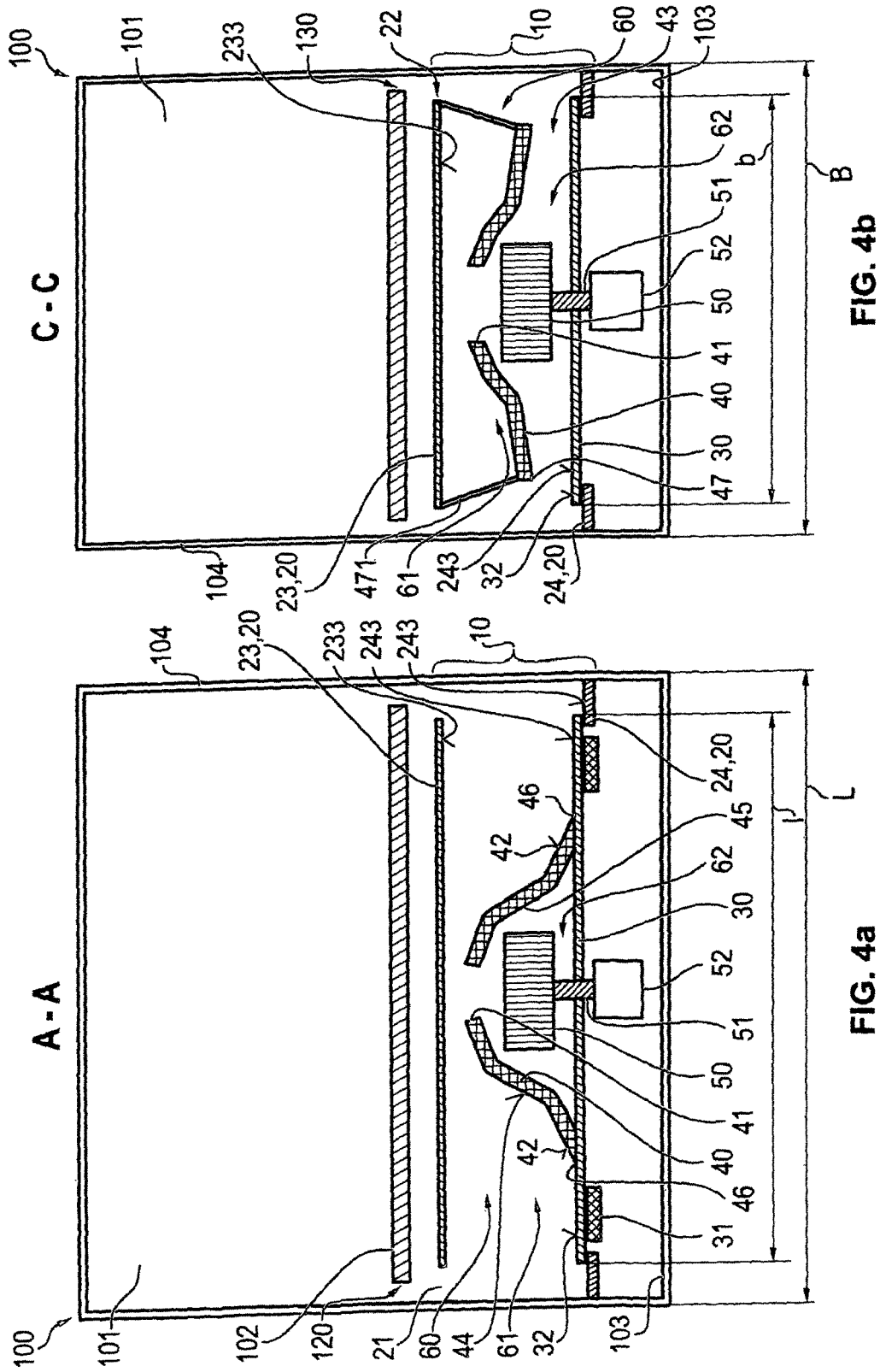
FIG. 4*a* is a schematic cross section through an incubator according to the present invention with a heater according to FIG. 3 along section line A/A in FIG. 3.
FIG. 4b is a schematic cross section through an incubator according to the present invention with a heater according to FIG. 3 along the cross-section line C/C.
Figure 5:
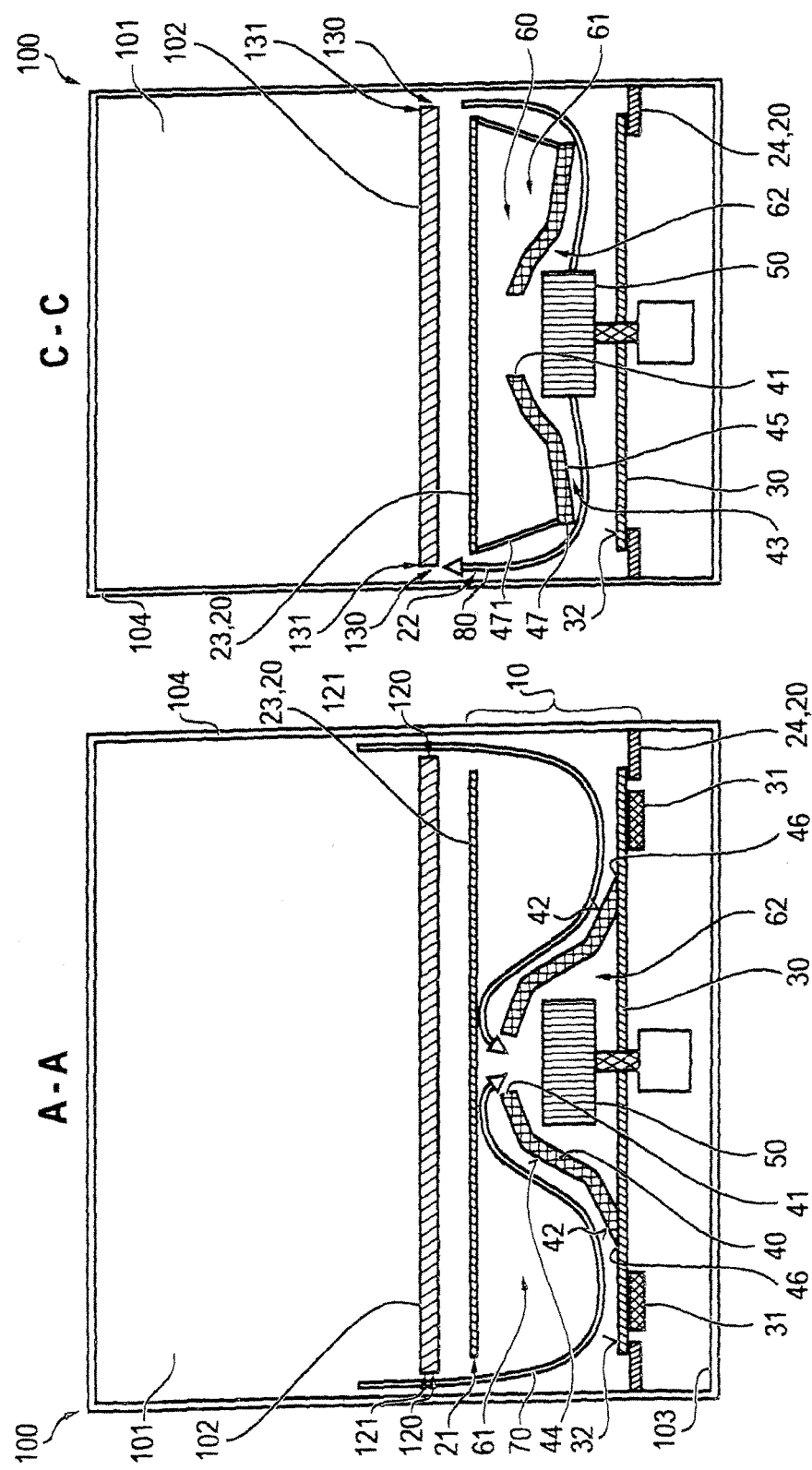

FIG. 4a, which shows a cross section through an incubator 100 according to the present invention along line A/A in FIG. 3, represents a schematic section through a heater 10 according to the present invention. The heater 10 is arranged in an incubator 100 according to the present invention under the reclining surface 102, on which the infant to be treated lies during the operation of the incubator 100. It is seen that the housing structure 20 is arranged in parallel to the reclining surface 102 of the incubator 100. In particular, the upper housing surface 233 and the lower housing surface 243 with the heat transfer element 30 are arranged in parallel to the reclining surface 102. In addition, the upper housing surface 233 and the lower housing surface 243 are also arranged in parallel to the bottom 103 of the incubator. The reclining surface 102 may be tilted in relation to the heater 10 by a certain angle, for example, for performing a Trendelenburg maneuver. This is especially useful when the infant, which is lying on the reclining surface, shall be turned. It is also conceivable that the bottom 103 does not represent a flat plane, but has an arch.

It is seen, furthermore, in FIG. 4a that the housing structure 20, namely, the upper housing surface 233 and the lower housing surface 243, define a flow space 60. This flow space 60 has an inflow space 61 and an outflow space 62. The flow space 60 is divided into the inflow space 61 and the outflow space 62 by means of the flow element 40. The fan impeller 50 of the heater 10 is arranged in the flow space 60, namely, in the outflow space 62. The fan impeller 50 is connected with a motor 52 via an axis 51. The motor 52 brings about rotation of the fan impeller 50 via the axis 51 when the heater 10 is in operation. The motor 52 is arranged under the lower housing surface 243.

It is seen, furthermore, that the lower housing surface 243 carries the heat transfer element 30. The heat transfer element 30 forms a large part of the lower housing surface 243. The surface 32 of the heat transfer element 30 forms a part of the lower housing surface 243 in this case as well. Two heating elements 31 are arranged under the heat transfer element 30. However, it is also conceivable that only one heating element 31 or a plurality of heating elements 31 are arranged under the heat transfer element 30. The heating element 31 is preferably a heating cartridge. The heating cartridge releases its heat direction to the heat transfer element 30. The heat transfer element 30 is preferably designed in this case such that it is a good heat conductor. For example, the heat transfer element 30 may consist of aluminum, temperature-resistant plastic with good thermal conductivity or another material having good thermal conductivity. As a consequence, the entire surface 32 of the heat transfer element 30 is brought to a certain surface temperature by the heating elements 31 during the operation of the heater.

The flow element 40 shown in FIG. 4a has, as was already described above (cf. FIG. 3), a passage opening 41, through which the inflowing air stream can enter the outflow space 62 from the inflow space 61. It is also seen in this case that the flow element 40 has a surface 44 and an underside 45. The surface 44 defines the inflow space 61. The underside 45 defines the outflow space 62. As a consequence, the inflow space 61 is defined at least by the upper housing surface 233, the surface 32 of the heat transfer element 30 and the surface 44 of the flow element 40. The outflow space 62 is defined at least by the top side 32 of the heat transfer element 30 and the underside 45 of the flow element 40.

The flow element 40 has, furthermore, as was already described in connection with FIG. 3, an edge 46, which is in tight, especially sealing contact with the surface 32 of the heat transfer element 30. A tight contact is a contact with which the edge 46 is formed so close to the surface 32 of the heat transfer element 30 that the inflowing air stream 70 does not flow through between the edge 46 and the surface 32. In other words, the flow element 40 prevents the inflowing air from being able to flow through between the surface 32 of the heat transfer element 30 and the edge 46 of the flow element 40. The flow element 40 forms an inflow barrier 42 for the inflowing air stream in this manner.

It is seen, furthermore, in FIG. 4a that the length l of the heat transfer element 30 corresponds essentially to the length L of the bottom 103 or to the base of the incubator 100, as it was defined above.

An air inlet 21 each is formed on both sides for the entry of the inflowing air stream into the heater 10 between the housing structure 20 and the outer wall of the incubator 100. To guide the air from the incubator chamber 101 to this air inlet 21, suction slots 120 are formed on the side 121 of the reclining surface 102.

The above-described heater 10, which is shown schematically in FIG. 4a, is also seen in FIG. 4b, which shows a cross section through an incubator 100 according to the present invention along line C/C in FIG. 3. As was shown already, the upper housing surface 233 and the lower housing surface 243 with the heat transfer element 30 define the flow space 60. The air outlets 22 are shown on the sides of the upper housing surface 233 in this cross section. These are used to return the heated air from the heater 10 to the incubator chamber 101. To guide the air from the air outlet 22 to the incubator chamber 101, a diffusion slot 130 each is formed between the side 131 of the reclining surface 102.

It is seen, furthermore, in FIG. 4b that the edge 47 of the flow element 40 has no contact with the surface 32 of the heat transfer element 30. The outflow guide 43 is formed between the edge 47 and the surface 32. The heated air coming from the outflow space 62, namely, the outflowing air stream (cf. FIG. 5b), can flow through this outflow opening 43 to the air outlets 22. The flow element 40 has another edge 471, which is in contact with the upper housing surface 233 and prevents a fluidic short-circuit between the inflow space 61 and the outflow space 62 in the area of the outflow guide. However, it is also conceivable that the flow element 40 is designed without this additional edge 471.

It is seen, furthermore, that the width b of the heat transfer element 30 corresponds essentially to the width B of the base 103 of the incubator 100.

It is seen in FIG. 5a that the outflowing air stream 70 is coming from the incubator chamber 101 of the incubator 100. This is air that shall be fed to the heater 10 for repeated heating. This inflowing air stream 70 flows on the side 121 of the reclining surface 102 through a suction slot 120, which is formed between the reclining surface 102 and the wall of the incubator 100. The inflowing air stream 70 flows from there through the air inlet 21 and into the flow space 60 of the heater 10. The air inlet 21 is formed between the upper housing element 23 and the side wall 104 of the incubator 100. The air inlet 21 may also be formed between the flow element 40 and the upper housing element 23 in an alternative embodiment. It is also conceivable that the air inlet 21 is formed between the flow element 40 and the housing wall, e.g., the side wall 104, of the incubator 100. At least one part or section of the flow element 40 extends to the side wall 104 of the incubator 100 in this case. However, the inflow space 61 is defined in any case by the flow element 40, the upper housing element 23, namely, the upper housing surface 232, and the surface 32 of the heat transfer element 30. The inflowing air stream 70, which has flown into the inflow space 61, is sent over the surface 32 of the heat transfer element 30 and heated in the process. The inflowing air stream 70 is then guided further over the inflow barrier 42 formed by the flow element 40 to the passage opening 41. The inflowing air stream 70 flows at the passage opening 41 to the fan impeller 50 and into the outflow space 62.

The air stream 70 having flown in before is now called an outflowing air stream 80 in the outflow space 62. In other words, the inflowing air stream 70 flows through the inflow space 61, the outflowing air stream 80 flows through the outflow space 62 and the inflowing air stream 70 passes over into the outflowing air stream 80 in the area of the passage opening 41, which connects the inflow space 61 and the outflow space 62 with one another.

It is seen in FIG. 5b that the outflowing air stream 80 is then guided again from the fan impeller 50 over the surface 32 of the heat transfer element 30 and under the underside 45 of the flow element 40 back to the air outlet 22 through the outflow guide 43. The outflowing, heated air stream 80 reaches air slots 130 from there. These air slots 130 are formed between the side 131 of the reclining surface 102 and the side wall 105 of the incubator 100. The incoming heated air stream 80 then rises up like a curtain on the side wall 105 and thus reaches the incubator chamber 101. The edge 471, which is optionally present, prevents a fluidic short-circuit between the inflow space 61 and the outflow space 62 in this case as well.

Figure 6:
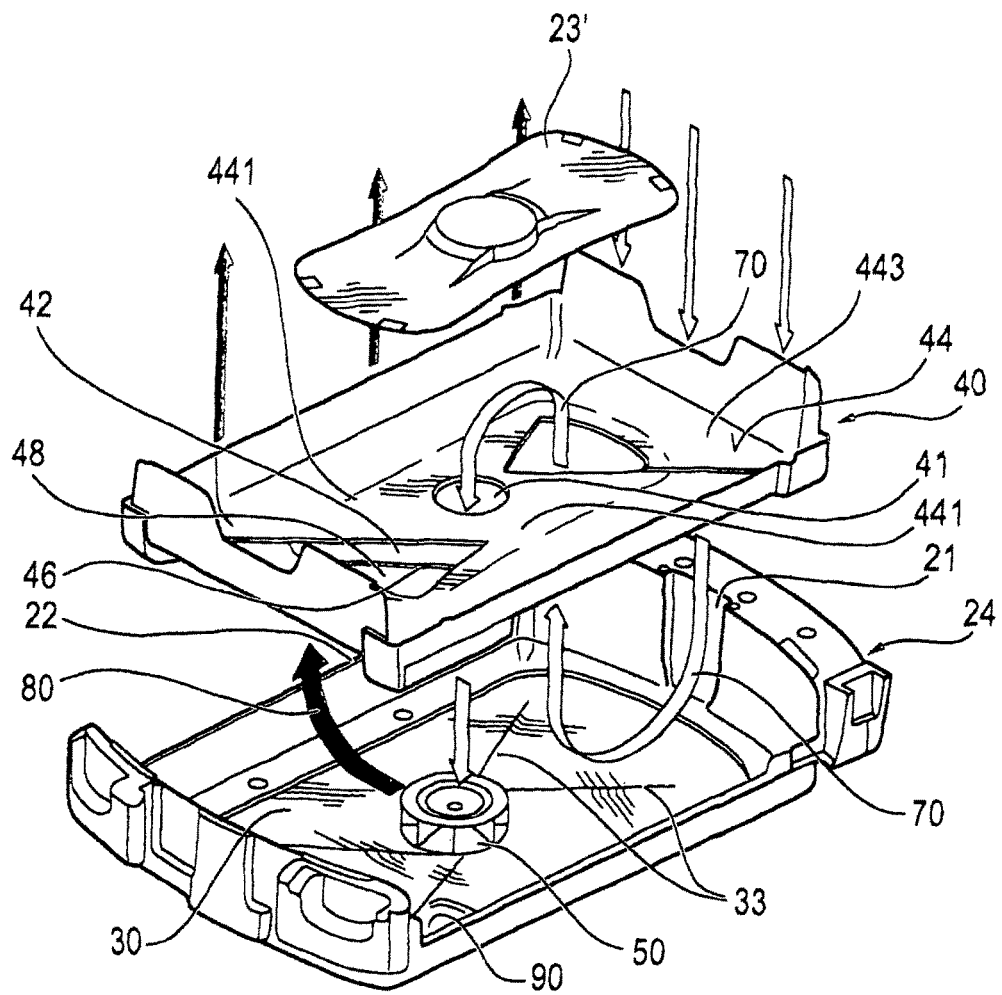
FIG. 6 is an exploded view of an embodiment of a heater according to the present invention.

It is seen in the exemplary embodiment shown in FIG. 6 that the housing elements 23', 24, the flow element 40' and the heat transfer element 30 of the heater 10 have each an at least partially arched shape. The flow element 40' has a fastening section 443. The fastening section encloses an inner section 441 and extends in the mounted state up to the wall (not shown) of the incubator. The flow element 40' is arranged between the upper housing element 23' and the lower housing element 24 in this case as well. The upper housing element 40' is designed as a cover element and is placed on the flow element 40'. The upper housing element 23' can thus also be called a cover element 23'.

Besides the passage opening 41, the flow element 40' has, furthermore, two additional passage openings 48, which are arranged symmetrically in relation to one another. An inflow barrier 42 each is formed in the area of these passage openings 48. The edges 46 of the inflow barriers 42 are in positive-locking, sealing connection in the mounted state with sealing elements 33, which are formed on the heat transfer element 30.

The inflow space 61 is divided into two sections in this exemplary embodiment. The first section is defined by the underside 45 of the flow element 40' and the lower housing surface 243. It extends from the air inlet 21 to the inflow barrier 42 in each case. The second section is defined by the top side 44 of the flow element 40' and the underside 232 of the upper housing element 23'. It extends from the additional passage openings 48 to the passage opening 41.

The heat transfer element 30 has, furthermore, a water of condensation collection site 90 in the exemplary embodiment shown in FIG. 6. This water of condensation collection site 90 is located at a low site of the incubator 100 during the operation of the incubator 100, so that liquid being formed in the incubator 100 can flow down to this site. It is thus recognized in FIG. 6 that the water of condensation collection site 90 is a slight depression in the surface 32 of the heat transfer element 30. The depression is bend-like and thus represents no flow obstacle for the inflowing or outflowing air stream 70, 80. Water of condensation that may possibly be formed can collect in this depression, i.e., in the water of condensation collection site 90, because it is the lowest point of the surface 32 of the heat transfer element 30. However, since this surface 32 is heated according to the present invention, the water of condensation can again evaporate there rapidly. The surface 32 of the heat transfer element 30 can also be wiped off easily, for example, when the heater 10 is taken apart for cleaning purposes, so that water of condensation, which has possibly collected there, can be easily wiped off.

In any case, it is seen that it is advantageous in a heater 10 for an incubator for infants 100, wherein the heater 10 has a housing structure 20 with an upper housing surface 233 and with a lower housing surface 243, at least one air inlet 21 for an inflowing air stream 70, at least one air outlet 22 for an outflowing air stream 80, at least one fan impeller 50, at least one heating element 31 and at least one heat transfer element 30, wherein the upper housing surface 233 and the lower housing surface 243 define a flow space 60, if the heat transfer element 30 is a surface with a flat surface 32, which is arranged horizontally during the operation of the heater. It is also especially favorable in this connection if heat generated by the heating element 31 can be transferred by means of the heat transfer element 30 to both the inflowing air stream 70 and the outflowing air stream 80. The heat transfer element 30 may form the lower housing surface 24 entirely or partially.

It is seen, further, that it is advantageous if the heater 10 has a flow element 40, 40'. It is especially favorable in this connection if the flow element 40 divides the flow space 60 into an inflow space 61 and an outflow space 62. The flow element 40 may be arranged according to the present invention between the upper housing surface 233 and the lower housing surface 243. For example, the flow element 40, 40' may be made in one piece with an upper housing element 23 and/or with a lower housing element 24.

It is especially expedient if the flow element 40,40' is designed such that it is suitable for guiding the air stream 70 flowing in from the air inlet 21 to the fan impeller and for guiding at the same time the air stream 80 flowing off from the fan impeller 50 to the air outlet 22. It is expedient if the flow element 40, 40' has a passage opening 41, through which the inflow space 61 and the outflow space 62 are connected with one another for flow.

Further, it is seen that it is advantageous if the heater 10 has a heated water of condensation collection site 90.

Further, it is seen that it is advantageous if an incubator for infants 100 with an above-described heater 10 has an incubator chamber 101 and a reclining surface 102. It is expedient in this case if the upper housing half 23 of the heater 10 is arranged under the reclining surface 102. It is expedient, furthermore, if the heater 10 is arranged in parallel to the reclining surface 102. It is especially advantageous if the incubator 100 has a base 103 with a length L and a width B, wherein the length l and the width b of the surface of the heat transfer element 30 of the heater 10 correspond essentially to the size of the length L and width B of the base 103 of the incubator 100.

It is seen, further, that it is expedient if suction slots 120 are formed on two mutually opposite first sides 121 of the reclining surface 102 for guiding the inflowing air stream 70 from the incubator chamber 101 to the heater 10 and if air slots 130 are formed on two mutually opposite second sides 131 of the reclining surface 102 for feeding the outflowing air stream 80 from the heater 10 into the incubator chamber 101.

While specific embodiments of the invention have been shown and described in detail to illustrate the application of the principles of the invention, it will be understood that the invention may be embodied otherwise without departing from such principles.

The invention claimed is:

1. A heater for an incubator, the heater comprising:
   a first wall;
   a second wall spaced from said first wall, said first and second walls defining a flow space;
   a flow element arranged in said flow space, and dividing said flow space into an inflow space and an outflow space, said first wall, said second wall, and said flow element defining said inflow space, said second wall and said flow element defining said outflow space, said flow element defining an opening between said inflow and outflow spaces;
   a fan arranged in said flow space and configured to move a flow stream from said inflow space to said fan, and to move the flow stream from said fan to said outflow space;
   a heating element arranged on said second wall and configured to generate heat, said heating element arranged and configured to transfer heat generated by said heating element to said second wall, said second wall being arranged to transfer heat generated by said heating element to the flow stream in said inflow space, and to also transfer heat generated by said heating element from said second wall to the flow stream in said outflow space.

* * * * *